US008107635B2

(12) United States Patent
Ludvigsen

(10) Patent No.: US 8,107,635 B2

(45) Date of Patent: Jan. 31, 2012

(54) AUDITORY PROSTHESIS, A METHOD AND A SYSTEM FOR GENERATION OF A CALIBRATED SOUND FIELD

(75) Inventor: Carl Ludvigsen, Valby (DK)

(73) Assignee: Widex A/S, Lynge (DK)

( * ) Notice: Subject to any disclaimer, the term of this patent is extended or adjusted under 35 U.S.C. 154(b) by 1846 days.

(21) Appl. No.: 10/201,263

(22) Filed: Jul. 24, 2002

(65) Prior Publication Data

US 2003/0002698 A1 Jan. 2, 2003

Related U.S. Application Data

(63) Continuation-in-part of application No. PCT/DK01/00048, filed on Jan. 23, 2001, now abandoned.

(30) Foreign Application Priority Data

Jan. 25, 2000 (DK) ................................ 2000 00113

(51) Int. Cl.

*H04R 29/00* (2006.01)
*H04R 25/00* (2006.01)
*H04R 5/00* (2006.01)
*A61B 5/12* (2006.01)
*A61B 5/00* (2006.01)

(52) U.S. Cl. ............ 381/60; 381/314; 381/317; 381/17; 381/56; 381/312; 73/585; 600/559

(58) Field of Classification Search .................... 381/60, 381/312, 314, 317, 1, 17–19, 56–58; 73/585; 600/559

See application file for complete search history.

(56) References Cited

U.S. PATENT DOCUMENTS

| | | | | | |
|---|---|---|---|---|---|
| 3,922,506 | A | * | 11/1975 | Frye | 381/60 |
| 4,065,647 | A | * | 12/1977 | Frye et al. | 381/60 |
| 4,548,082 | A | * | 10/1985 | Engebretson et al. | 73/585 |
| 4,577,641 | A | | 3/1986 | Hochmair et al. | |
| 4,615,007 | A | * | 9/1986 | King et al. | 600/559 |
| 4,992,966 | A | * | 2/1991 | Widin et al. | 702/103 |
| 5,046,102 | A | * | 9/1991 | Zwicker et al. | 381/317 |
| 5,386,478 | A | * | 1/1995 | Plunkett | 381/103 |
| 5,645,074 | A | | 7/1997 | Shennib et al. | |
| 5,991,417 | A | | 11/1999 | Topholm | |
| 6,094,489 | A | * | 7/2000 | Ishige et al. | 381/60 |

(Continued)

FOREIGN PATENT DOCUMENTS

EP 0 341 995 B1 8/1995

(Continued)

OTHER PUBLICATIONS

Applicant's admitted prior art, Figure 1, p. 7, lines 5-19.*

*Primary Examiner* — Devona Faulk

(74) *Attorney, Agent, or Firm* — Sughrue Mion, PLLC

(57) ABSTRACT

An auditory prosthesis (14, 14') is adapted for compensation of hearing loss and for sound pressure determination. During calibration of the sound field to be used during fine-tuning of the auditory prosthesis, the auditory prosthesis is positioned at an observation point in the sound field, and the sound pressure at the auditory prosthesis is adjusted based on determinations of sound pressures performed with the auditory prosthesis. Thus, the need for dedicated calibrated sound pressure determining equipment is eliminated. The invention provides an auditory prosthesis, a method and a system for calibration of a sound field.

24 Claims, 5 Drawing Sheets

U.S. PATENT DOCUMENTS

| | | | | |
|---|---|---|---|---|
| 6,154,546 | A * | 11/2000 | Uvacek | 381/60 |
| 6,195,438 | B1 * | 2/2001 | Yumoto et al. | 381/103 |
| 6,532,296 | B1 * | 3/2003 | Vaudrey et al. | 381/371 |
| 6,590,986 | B1 * | 7/2003 | Fazio | 381/314 |
| 6,654,652 | B1 * | 11/2003 | Dalton et al. | 700/94 |
| 2001/0005420 | A1 * | 6/2001 | Takagi et al. | 381/312 |
| 2001/0014818 | A1 * | 8/2001 | Kennedy | 607/57 |

FOREIGN PATENT DOCUMENTS

| | | | |
|---|---|---|---|
| WO | WO 98/47313 | A2 | 10/1998 |
| WO | WO 99/48323 | A2 | 9/1999 |

* cited by examiner

AUDITORY PROSTHESIS, A METHOD AND A SYSTEM FOR GENERATION OF A CALIBRATED SOUND FIELD

RELATED APPLICATIONS

The present application is a continuation-in-part of application No. PCT/DK01/00048, filed on 23 Jan. 2001 in Denmark, now abandoned. The present application is based on PA 2000 00113, filed on 25 Jan. 2000 in Denmark, the contents of which are incorporated hereinto by reference.

BACKGROUND OF THE INVENTION

1. Field of the Invention

The present invention generally relates to auditory prostheses. The invention more particularly relates to a method and a system for calibration of a sound field. The invention still more specifically relates to a method and a system to be used during fine-tuning of an auditory prosthesis.

An auditory prosthesis, such as a hearing aid, is typically fine-tuned to an individual user by placing the user with the auditory prosthesis in an auditory test room in which various sound fields are generated from a sound source. Each of the sound fields corresponds to a sound field occurring in a real life sound environment, such as in a concert hall, in an environment with party noise, with traffic noise, with no background noise, etc, etc. It is the object of the fine-tuning procedure to adjust the auditory prosthesis in such a way that the user's hearing loss is compensated as well as possible in similar real life sound environments.

In order to perform the required auditory measurements accurately during auditory prosthesis fine-tuning, the test room and the auditory fine-tuning equipment must be calibrated to provide a predetermined sound field at the position of the user. It is well known that sound pressure in sound fields generated with equipment that is not calibrated may vary significantly. Many dispensers of hearing aids constitute rather small entities for which investment in calibration equipment represents a significant burden.

2. The Prior Art

EP-A-0 341 995 discloses an auditory prostheses having a microphone, a signal processor, a signal output and an output transducer. The calibration device comprises a memory for storing information characteristic of information intrinsic to the individual auditory prosthesis and representing either a sufficient set of adjustment parameters for calculation of the transfer function of the auditory prosthesis or manufacturing information.

WO-A-9948323 relates to a hearing aid fitting method comprising selection of loudness levels for a plurality of frequencies and comparing each loudness level for each frequency for perceived sameness.

SUMMARY OF THE INVENTION

It is an object of the present invention to provide a method and a system for generation of a calibrated sound field that reduces calibration equipment requirements without substantially compromising calibration accuracy.

The invention, in a first aspect, provides an auditory prosthesis comprising a microphone for transforming an acoustic input signal into a microphone signal, a processor with a processor output and a measuring signal output, said processor being adapted for providing at said processor output a hearing loss compensation signal and for providing at said measuring signal output a sound level signal determined on the basis of the microphone signal, and an output transducer for transforming the hearing loss compensation signal into an acoustic output signal.

This permits use of resources already available in the auditory prosthesis for calibration of equipment used to generate the sound field corresponding to a specific sound environment for use during fine-tuning. Thus, utilisation of the auditory prosthesis for sound pressure determinations eliminates a need for dedicated sound pressure determining equipment Hearing defects may typically vary as a function of frequency in a way that is different for each individual user. To take account of this, an advantageous embodiment of the auditory prosthesis of the invention may be provided, where the auditory prosthesis further comprises a filter bank in the signal processor connected with the microphone to receive the microphone signal therefrom, said filter bank having bandpass filters for dividing the microphone signal into a set of bandpass filtered microphone signals, wherein the signal processor is adapted to generate the processor output signal by individually processing each of the bandpass filtered microphone signals, summing the processed signals to form the processor output signal and determine sound pressures based on the set of bandpass filtered microphone signals.

Hereby, selective calibration of the equipment for sound field generation in each of the frequency bands of the auditory prosthesis is facilitated. Further, a need for a dedicated frequency analyser is eliminated. In the following, the frequency ranges of the bandpass filters are also denoted channels.

The auditory prosthesis may contain more than one microphone, e.g. for provision of directional characteristic capabilities, noise suppression capabilities, etc.

Preferably, sound pressure is determined as a sound pressure level in accordance with an accepted standard, such as ISO 131-1979, Acoustics—Expression of physical and subjective magnitudes of sound or noise in air. The sound pressure level is the sound pressure relative to a reference pressure, typically 20 μPa, preferably in dB.

As mentioned above, utilisation of an auditory prosthesis for sound pressure determinations eliminates a need for dedicated sound pressure determining equipment, such as a calibrated microphone with a measuring apparatus for determination of sound pressure, e.g. a sound level meter according to IEC 651-1979, Sound level meters.

The auditory prosthesis may comprise a memory for storing sensitivity values of the microphone. The sensitivity may be the sound pressure level sensitivity. Sensitivity is defined as the ratio of generated electronic microphone signal magnitude to applied sound pressure. The magnitude may be the amplitude, RMS-value, etc. Typically, a set of sensitivity values is stored for a set of respective frequency ranges, and the stored sensitivity values are used in the determination of sound pressure.

The sensitivity values specified on the data sheet provided by the manufacturer of the microphone may be stored in the memory.

Typically, sound pressure determinations made by auditory prostheses vary 1-2 dB so that calibration of sound field generating equipment with an auditory prosthesis according to the present invention may reduce sound pressure variations, e.g. from app. 20 dB to app. 2 dB. Typically, a 2 dB sound pressure ambiguity is sufficiently accurate for the purpose of performing an optimum fine-tuning of an auditory prosthesis.

In a preferred embodiment of the present invention, a calibration of the microphone of the auditory prosthesis is performed for determination of sensitivity values of the microphone, and the determined sensitivity values are stored in the memory. Calibration of the sound field with an auditory prosthesis according to this embodiment is substantially as accurate as the calibration accuracy of the microphone.

The invention, in a second aspect, provides a method for generation of a calibrated sound field, comprising the steps of positioning in a test space an auditory prosthesis, said auditory prostheses having a microphone, a signal processor, and an output transducer, said auditory prostheses being adapted to provide a sound level signal determined on the basis of a signal from said microphone, generating a sound field in the test space, and feeding the sound level signal to the controller in order that the controller may modify the generated sound field based on the sound level signal as appropriate to generate a calibrated sound field.

In a preferred embodiment of the method, the step of positioning further comprises the steps of positioning the auditory prosthesis in the ear of a user situated in the test space.

When the auditory prosthesis is positioned in the ear of a user who is situated in the test space during sound field calibration, the need for a manikin or a test dummy, an occluded ear simulator, etc, is eliminated.

The method may further comprise the step of modifying the generated sound field based on the generated set of sound pressure signals whereby a calibrated sound field is generated. Thus, in the method the step of generating a sound field may comprise the steps of providing a sound signal, modifying the sound signal according to a set of control parameters to provide a modified sound signal, and transforming the modified sound signal into a sound field in the test space. The method may further comprise the steps of supplying the set of sound pressure signals to a controller for calculation of new values of the set of control parameters for modification of the sound signal.

The invention, in a third aspect, provides a system for generation of a calibrated sound field, comprising a sound signal generator for generation of a sound signal, a sound signal modifier adapted to modify the sound signal in accordance with a set of control parameters for provision of a modified sound signal, a sound transducer for transforming the modified sound signal into a sound field in a test space, an auditory prosthesis, and a controller, wherein said auditory prostheses has a microphone for transforming an acoustic input signal into a microphone signal, a processor with a processor output and a measuring signal output, wherein said processor is adapted for providing at said measuring signal output a sound level signal determined on the basis of the microphone signal, and wherein said controller is adapted to receive the sound level signal and to calculate a new set of control parameters based on the sound level signal.

It is not required to calibrate the sound field generating equipment before every fine-tuning of an auditory prosthesis to a user. Typically, it is sufficient to calibrate at regular intervals, e.g. during the first fine-tuning of a working day. However, when the sound field is calibrated with the auditory prosthesis worn by the user to whom the auditory prosthesis is subsequently fine-tuned, the additional advantage is obtained that the sound field is calibrated at the position of the auditory prosthesis during fine-tuning whereby ambiguity of sound pressure at the auditory prosthesis during fine-tuning is minimised.

The auditory prosthesis may be a hearing aid that is adapted to be programmed by an external programming device and to be connected to the programming device with a programming cable. Preferably, the signal output is also adapted to be connected to the programming cable, in order that the sound level signal can be supplied to the controller via the programming cable.

The auditory prosthesis may further comprise a wireless communication link for reception of the set of sound pressure signals from the signal processor and for transmission of corresponding respective signals.

The sound signal may be generated by reproduction of a signal recorded in a storage medium.

The controller may be comprised in a personal computer comprising a memory for storage of the control parameters together with a computer programme for calculation of the control parameters, the computer further comprising input means for receiving the set of sound pressure signals.

BRIEF DESCRIPTION OF THE DRAWINGS

In the following the invention will be further explained with reference to the accompanying drawing wherein.

DESCRIPTION OF THE PREFERRED EMBODIMENTS

Figure 1:
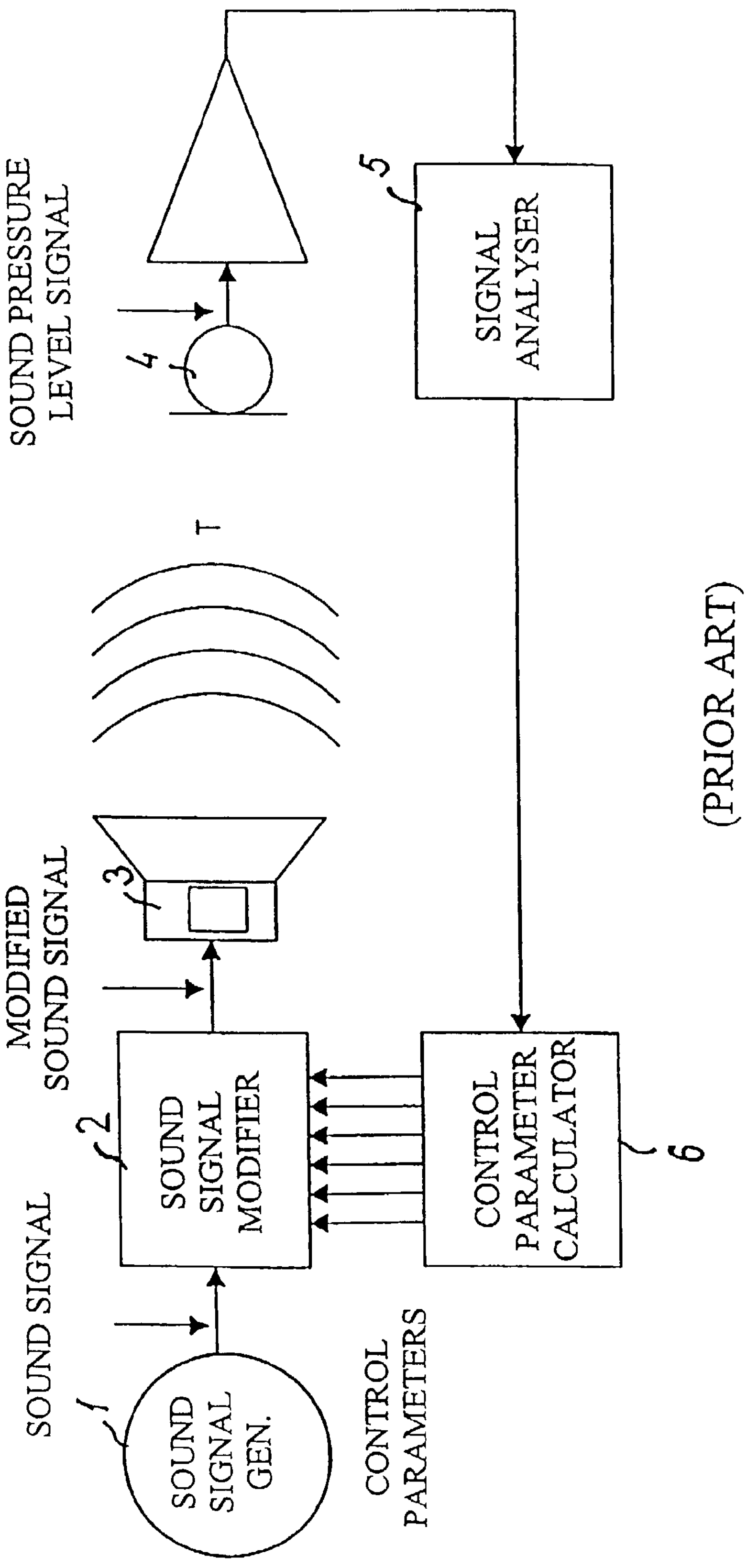
(PRIOR ART) FIG. 1
FIG. 1 is a block diagram of a prior art system for generation of a calibrated sound field.

A prior art sound field calibration system is shown in FIG. 1. A sound signal generator 1 generates a sound signal that is supplied to a sound signal modifier 2 wherein the level of the sound signal is modified as a function of frequency in accordance with a set of control parameters stored in a memory, not illustrated, in the sound signal modifier 2. The modified sound signal obtained from the signal modifier 2 is converted by a loudspeaker 3 into a sound field in a test space T.

The sound field is monitored in at least one observation point within the test space T by measuring means 4 comprising a precision calibrated microphone.

The measuring signal obtained from measuring means 4, including level and/or frequency spectrum information, is supplied to control means comprising a signal analyser 5 for derivation of data representing the sound characteristic of the sound field in the test space, from where the data are supplied to a control parameter calculator 6 for calculation of a new set of control parameters for use in the signal modifier 2.

Figure 2:
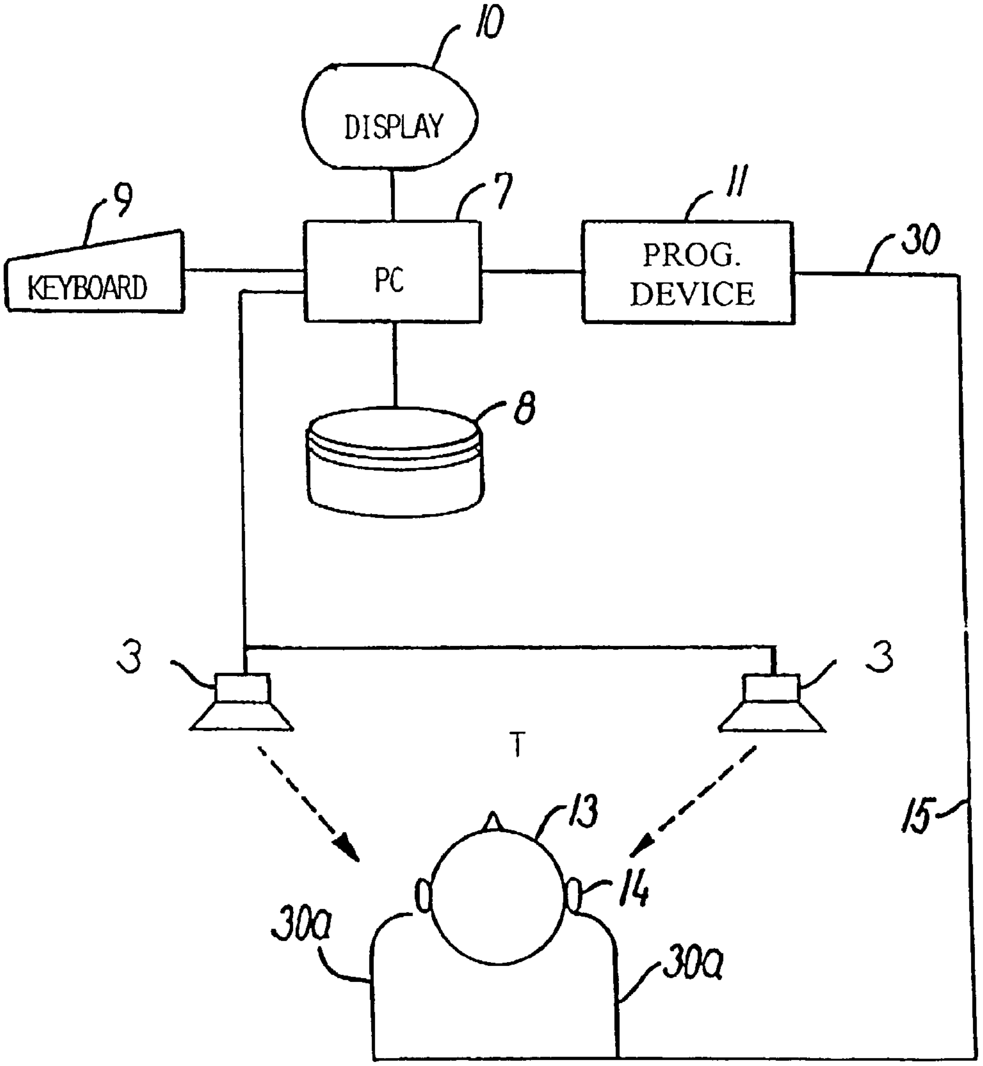
FIG. 2 is a block diagram of a first embodiment of the present invention.

In the embodiment of the present invention shown in FIG. 2, the sound signal generator 1, the signal modifier 2, and the control means including the measuring signal analyser 5, and the control parameter calculator 6 of the system illustrated in FIG. 1 have been combined into a computing device 7, such as a personal computer, comprising memory means 8, such as a hard disc, a keyboard 9, a display screen 10, and a sound interface that is connected with loudspeakers 12 for conversion of the sound signal into a sound field in the test space T.

As further shown in FIG. 2 and in accordance with the invention, monitoring of the sound field in the test space T is performed by a microphone positioned in a hearing aid that is carried by a user 13 who is seated in the test space T. The measuring signal obtained from one of or both of the hearing aids 14 is transmitted to the computer 7 through a cable 15, preferably the programming cable 15 that is connected to a programming device 11 for programming of the hearing aid to suit various sound environments or listening situations by a computer assisted fine-tuning procedure.

Thereby the sound field calibration of the test space T and the fine-tuning procedure may be combined into a single sequential operation using the same computer system 7 for the sound field calibration of the test space and for the fine-tuning procedure.

Figure 3:
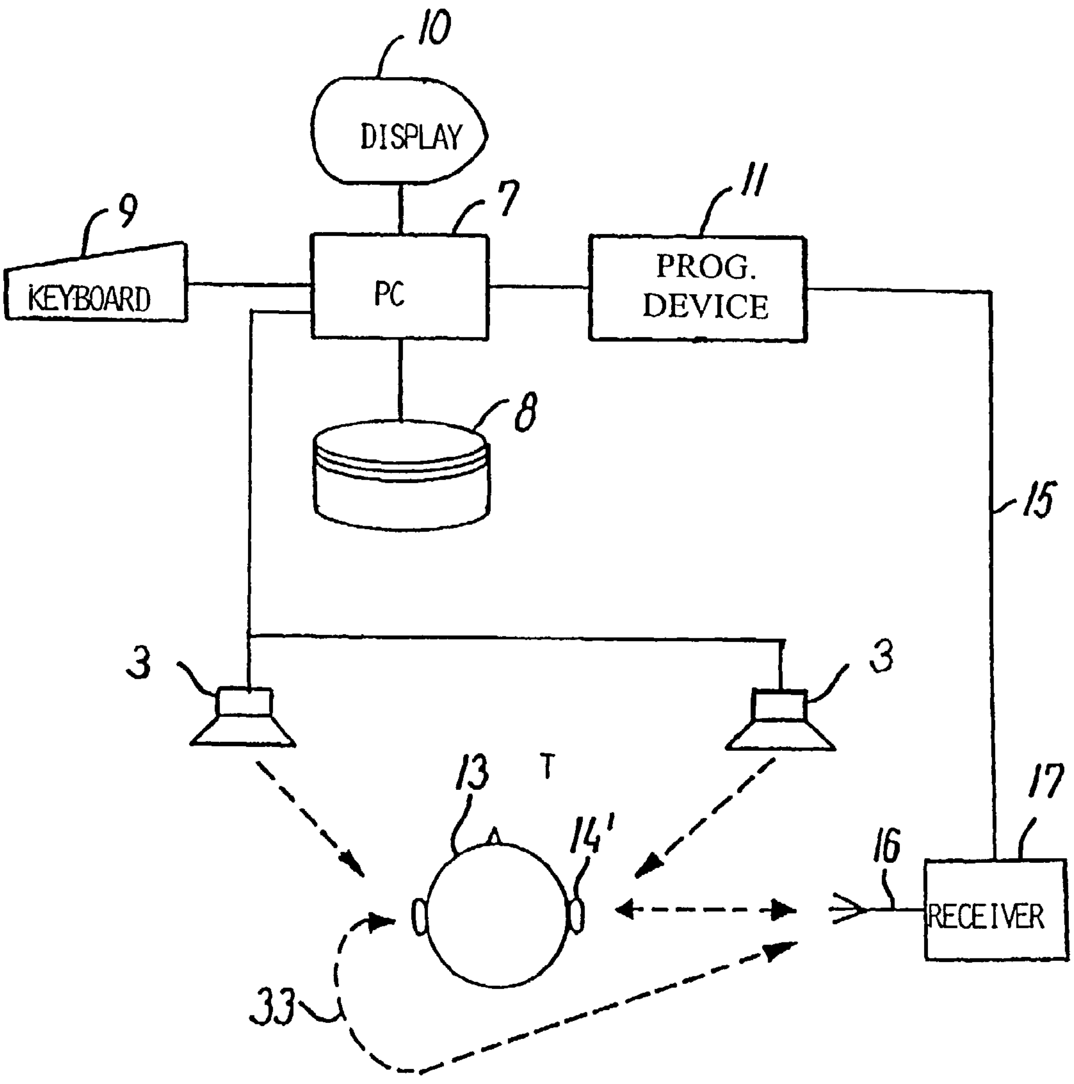
FIG. 3 is a block diagram of a second embodiment of the present invention.

In an alternative embodiment of the present invention shown in FIG. 3, the measuring signal obtained from the hearing aids 14' is supplied to the computer 7 by wireless transmission means, such as IR or radio transmission from transmitters, not shown, integrated in each hearing aid 14', to an antenna 16 connected with a receiver 17 that is also connected to the cable 15.

In order to avoid possible discomfort to a user 13 during the calibration procedure, a pre-adjustment of the sound signal may be performed prior to calibration. During the pre-adjustment the hearing aid is positioned at the observation point in the test space T without being carried by the user whereby the need for adjustment of the sound signal during calibration is minimised in order to minimise possible user discomfort.

Figure 4:
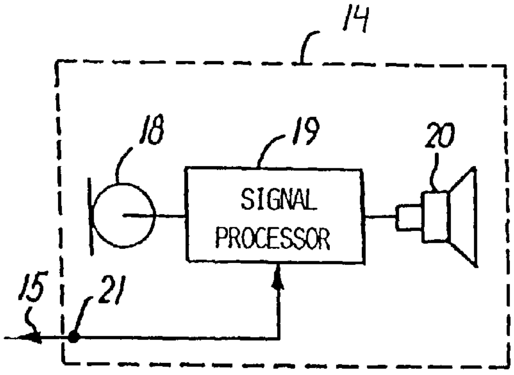
FIG. 4 is a block diagram of an embodiment of a hearing aid according to the present invention.

In the simplified block diagram shown in FIG. 4, a hearing aid 14 for use in the implementation of the calibration method and system according to the invention comprises at least one microphone 18 connected with a signal processor 19, preferably comprising programmable signal processing parts, such as bandpass filters and amplifiers, from which a processor output signal is supplied to an output transducer 20, such as a hearing aid receiver.

It will be obvious for the person skilled in the art that the circuits shown in FIG. 4 may be realised using digital or analogue circuitry or any combination hereof. In the present embodiment, digital signal processing is employed and thus, the processor 19 comprises digital signal processing circuits. In the present embodiment, all the digital circuitry of the hearing aid may be provided on a single digital signal processing chip, or, the circuitry may be distributed on a plurality of integrated circuit chips in any appropriate way.

According to the invention, the hearing aid 14 also comprises interface means that is connected to the signal processor 19 for outputting the processor output signal. The interface means may comprise a coupling terminal 21 for connection with the cable 15 as shown in FIG. 2, and the interface means may comprise wireless interface means as illustrated in FIG. 3.

In a programmable hearing aid according to the present invention, a bi-directional communication link may be provided between the signal processor 19 and the computer 7 as shown in FIGS. 2 and 3. Thus, data may flow in both directions in signal line 15 shown in FIGS. 2 and 3. For a non-programmable hearing aid, it is sufficient to provide a unidirectional communication link between the processor 19 and the computer 7 for transmission of the measuring signal to the computer 7 for use in the calculation of calibration control parameters.

Figure 5:
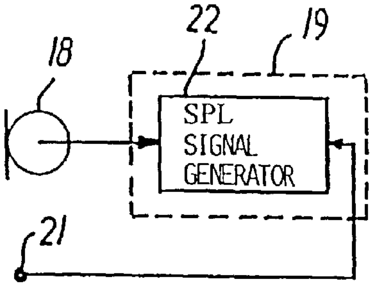
FIG. 5 is a block diagram of an embodiment of the signal processor of a hearing aid according to the present invention.

As shown in FIG. 5, the signal processor 19 comprises a sound pressure level signal generator 22 that is connected to the coupling terminal 21 for generation of the measuring signal. In a programmable hearing aid, the sound pressure level signal generator may also serve as input/output interface for communication of programming data between the signal processor 19 and the programming computer.

Figure 6:
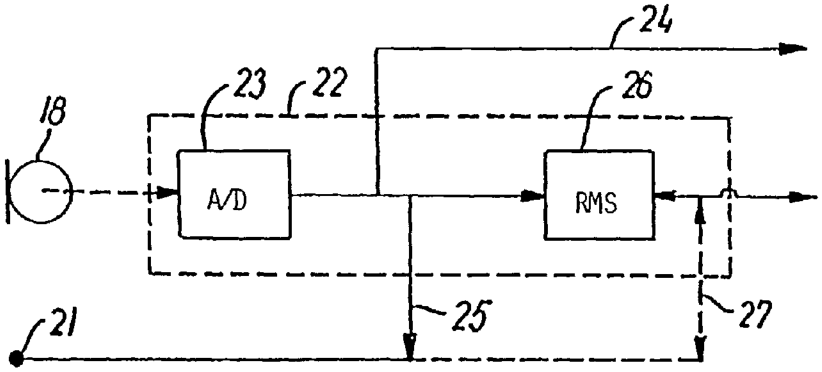
FIG. 6 is a block diagram of a signal processor of the hearing aid shown in FIG. 2 or 3.

As further illustrated in FIG. 6, the sound pressure level signal generator 22 may comprise an A/D converter 23 for provision of a digital measuring signal for use in further signal processing in the processor 19, as indicated by line 24, and for use in the calibration of the sound field.

The measuring signal may be provided directly from the A/D converter 23 to the interface means, e.g. the coupling terminal 21 as shown by the solid line 25, or, it may be further processed, e.g. averaged values may be calculated, and provided to the interface means. In another embodiment of the invention, a digital RMS-averaged signal is formed in a RMS-detector 26 and supplied to the interface means, e.g. the coupling terminal 21, via the dashed line 27.

Figure 7:
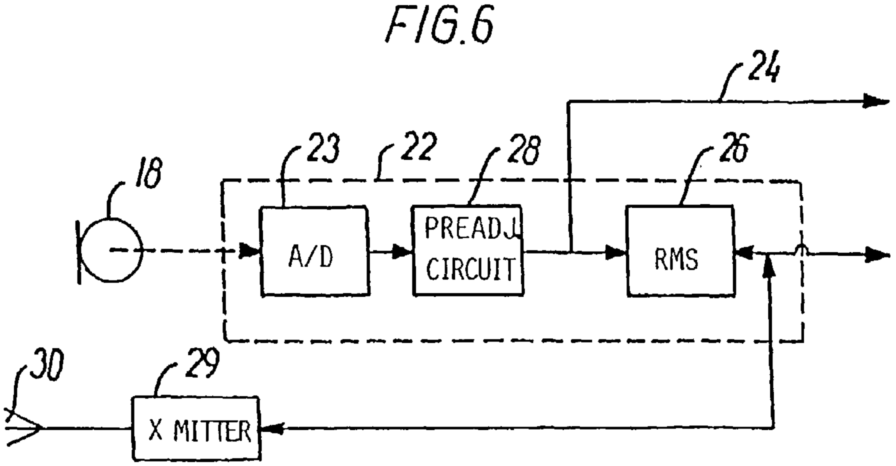
FIG. 7 is a block diagram of another signal processor of the hearing aid shown in FIG. 2 or 3.

As shown in FIG. 7, the measuring signal processor 22 may also include a pre-adjustment circuit 28 that is interconnected between the A/D converter 23 and the RMS detector 26 to provide pre-adjustment of the digital microphone signal into a calibrated microphone signal. The pre-adjustment circuit 28 comprises a memory for storing sensitivity values, such as sound pressure level sensitivity values, of the microphone defining ratios of electronic microphone signal amplitude to sound pressure at the microphone. Typically, a set of sensitivity values is stored for a set of respective frequency ranges, and the stored sensitivity values are used in the determination of sound pressure. The sensitivity values specified on the data sheet provided by the manufacturer of the microphone may be stored in the memory, or, sensitivity values as determined by a calibration measurement of the microphone 18 may be stored in the memory.

In the embodiment of the present invention shown in FIG. 7, the measuring signal obtained from the RMS detector 26 is supplied to a transmitter 29 feeding an antenna 30 positioned at the hearing aid 14, 14' for wireless transmission of the measuring signal to the antenna 16 and the receiver 17 shown in FIG. 3.

Figure 8:
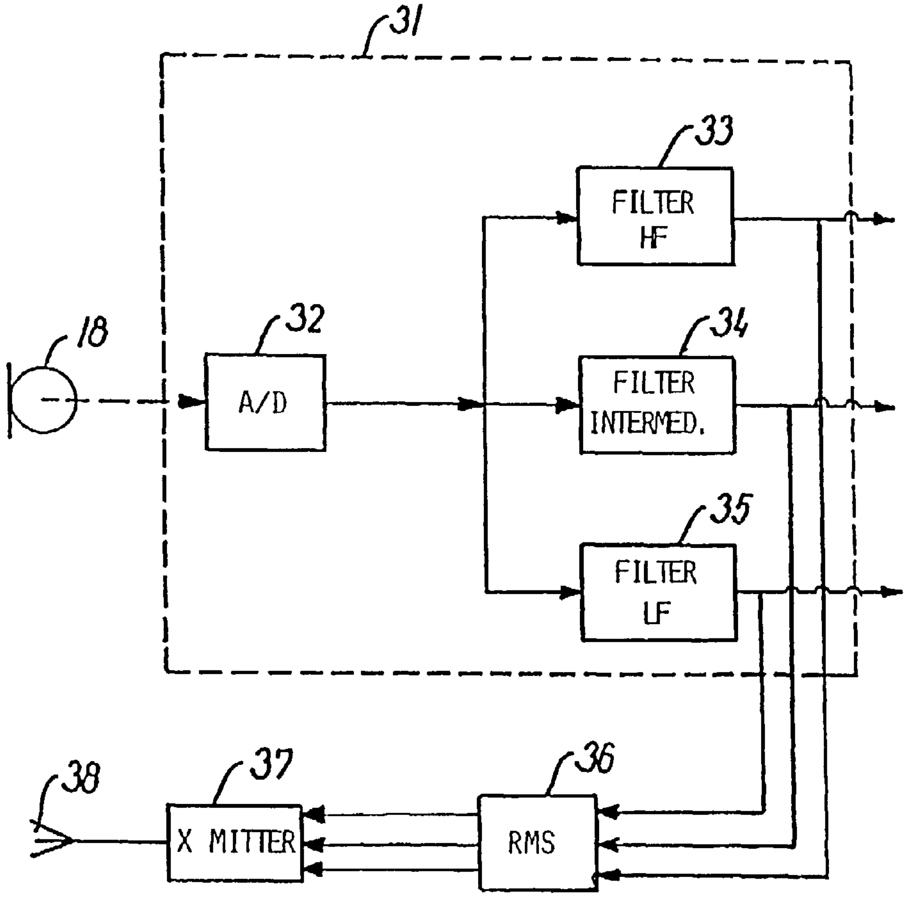
FIG. 8 is a block diagram of a hearing aid according to the present invention comprising a multichannel signal processor.

Although the hearing aid 14, 14' in FIGS. 4-7 is illustrated as a single channel hearing aid, it should be understood that a hearing aid 14, 14' according to the present invention may contain any appropriate number of channels. A multichannel hearing aid according to the present invention, as shown in FIG. 8, comprises a multichannel processor 31 wherein a digital microphone signal supplied by the A/D converter 32 is filtered by adjustable band pass filters 33, 34, and 35 into, e.g. a high frequency signal, an intermediate signal and a low frequency signal. The filtered digital signals are further processed in separate processing channels of the signal processor 31. Obviously, any number of channels may be provided in the hearing aid 14, 14'. The hearing aid may comprise an RMS detector 36 that is also divided into separate processing channels for individually processing of the output signals from the band-pass filters. The individually processed signals are transmitted to the computer 7 for adjustment of the control parameters.

I claim:

1. An auditory prosthesis comprising:

a microphone for transforming an acoustic input signal into a microphone signal;

a processor with a processor output, said processor being adapted for providing at said processor output a hearing loss compensation signal;

an output transducer for transforming the hearing loss compensation signal into an acoustic output signal; and a measuring signal output terminal for providing a sound level signal externally from said auditory prosthesis for use by a sound field generator in generating a calibrated sound field, said sound level signal being other than said acoustic output signal and determined on the basis of the microphone signal.

2. The auditory prosthesis according to claim 1, wherein said signal processor is provided with a filter bank, said filter bank having bandpass filters for dividing the microphone signal into a set of bandpass filtered microphone signal derivatives, and wherein said signal processor is adapted to provide the sound level signal by individually processing each of the bandpass filtered microphone signal derivatives, and summing the signal derivatives to provide the sound level signal.

3. An auditory prosthesis comprising:

a microphone for transforming an acoustic input signal into a microphone signal;

a processor with a processor output, said processor being adapted for providing at said processor output a hearing loss compensation signal;

an output transducer for transforming the hearing loss compensation signal into an acoustic output signal;

a measuring signal output terminal for providing a sound level signal externally from said auditory prosthesis for use by a sound field generator in generating a calibrated sound field, said sound level signal being other than said acoustic output signal and determined on the basis of the microphone signal; and a memory for storage of sensitivity values of said microphone, and a pre-adjustment circuit for providing pre-adjustment of the microphone signal in order to provide a calibrated microphone signal.

4. The auditory prosthesis according to claim 1, comprising a transmitter for transmission of the sound level signal.

5. The auditory prosthesis according to claim 1, wherein said measuring signal output terminal comprises a means for connecting a programming cable.

6. The auditory prosthesis according to claim 1, wherein said sound level signal is a digital signal.

7. The auditory prosthesis according to claim 1, wherein said sound level signal represents a root-mean-square sound pressure.

8. The auditory prosthesis according to claim 1, comprising a bank of band-pass filters for processing the microphone signal and for providing as said sound level signal a set of band-pass filtered signals.

9. A method for generation of a calibrated sound field, comprising the steps of positioning in a test space a sound signal generator and an auditory prosthesis, said auditory prosthesis having a microphone responsive to sound in said test space, a signal processor, and an output transducer for generating a sound output, operating said sound signal generator to generate a sound field in the test space, operating said auditory prosthesis to provide a sound level signal other than said sound output and determined on the basis of a signal from said microphone, and feeding the sound level signal to a controller externally of said auditory prosthesis in order that the controller may modify the generated sound field based on the sound level signal as appropriate to generate a calibrated sound field in said test space.

10. The method according to claim 9, wherein said positioning step comprises the step of positioning the auditory prosthesis in the ear of a user situated in the test space.

11. The method according to claim 9, wherein the step of generating a sound field comprises the steps of providing a sound signal according to an initial set of control parameters, transforming the sound signal into a sound field in the test space, and supplying the sound level signal to a controller for calculation of a modified set of control parameters for modification of the sound signal.

12. The method according to claim 9, comprising selecting for the controller a personal computer provided with a memory for storage of a set of control parameters, and using the computer together with a computer program for calculation of a revised set of control parameters.

13. The method according to claim 9, comprising connecting the auditory prosthesis to an external programming device by means of a programming cable, and supplying the sound level signal to the controller via the programming cable.

14. The method according to claim 9, comprising using a wireless link in the auditory prosthesis for transmission of the sound level signal.

15. A method for generation of a calibrated sound field, comprising the steps of positioning in a test space a sound signal generator and an auditory prosthesis, said auditory prosthesis having a microphone responsive to sound in said test space, a signal processor, and an output transducer for generating a sound output, operating said sound signal generator to generate a sound field in the test space, operating said auditory prosthesis to provide a sound level signal other than said sound output and determined on the basis of a signal from said microphone, feeding the sound level signal to a controller externally of said auditory prosthesis in order that the controller may modify the generated sound field based on the sound level signal as appropriate to generate a calibrated sound field in said test space, and storing microphone sensitivity values as specified by the manufacturer of the microphone, and determining the sound level signal based on the stored sensitivity values.

16. A method for generation of a calibrated sound field, comprising the steps of positioning in a test space a sound signal generator and an auditory prosthesis, said auditory prosthesis having a microphone responsive to sound in said test space, a signal processor, and an output transducer for generating a sound output, operating said sound signal generator to generate a sound field in the test space, operating said auditory prosthesis to provide a sound level signal other than said sound output and determined on the basis of a signal from said microphone, feeding the sound level signal to a controller externally of said auditory prosthesis in order that the controller may modify the generated sound field based on the sound level signal as appropriate to generate a calibrated sound field in said test space, and storing microphone sensitivity values determined by a calibration of the microphone, and determining the sound level signal based on the stored sensitivity values.

17. The method according to claim 9, comprising performing prior to calibration a pre-adjustment of the sound signal, using the hearing aid positioned at a selected observation point in the test space.

18. A system for generation of a calibrated sound field, comprising a sound signal generator for generation of a sound signal, a sound signal modifier adapted to modify the sound signal in accordance with a set of control parameters for provision of a modified sound signal, a sound transducer for transforming the modified sound signal into a sound field in a test space, an auditory prosthesis, and a controller, wherein said auditory prosthesis has a microphone for transforming an acoustic input signal into a microphone signal, a processor with a processor output and a measuring signal output terminal, and a transducer responsive to said processor output for generating a compensated acoustic output to the ear of a wearer of said auditory prosthesis, wherein said processor is adapted for providing at said measuring signal output terminal a sound level signal other than said compensated acoustic output and determined on the basis of the microphone signal, and wherein said controller is adapted to receive the sound level signal and to calculate a new set of control parameters based on the sound level signal for use by said sound signal modifier.

19. The system according to claim 18, wherein said controller comprises a personal computer including a memory for storage of the control parameters together with a computer program for calculation of the control parameters, and input means for receiving the sound level signal.

20. The system according to claim 18, wherein said auditory prosthesis is connected to an external programming device via a programming cable, and wherein said measuring signal output terminal is connected to said programming device via said programming cable for the purpose of supplying the sound level signal to said programming device and from there to said controller.

21. The system according to claim 18, wherein said auditory prosthesis comprises a wireless link for transmission of the sound level signal.

22. The system according to claim 18, wherein said controller comprises a signal analyser for derivation of data representing the sound characteristic of the sound field in the test space.

23. An auditory prosthesis comprising a microphone for transforming an acoustic input signal into a microphone signal;

a signal processor provided with a processor output and a filter bank;

a transducer for providing a sound output to a user: and a measuring signal output terminal for providing a sound level signal externally from said auditory prosthesis, wherein said filter bank has bandpass filters for dividing the microphone signal into a set of bandpass filtered microphone signal derivatives, and wherein said signal processor is adapted to provide said sound level signal to said measuring signal output terminal, said sound level signal being other than said sound output and being determined by individually processing each of the bandpass filtered microphone signal derivatives, and summing the signal derivatives to provide the sound level signal.

24. An auditory prosthesis according to claim 23, wherein said sound level signal comprises a set of sound pressure signals corresponding to respective sound pressures based on said bandpass filtered signals, and wherein said audio prosthesis further comprises an output transducer for transforming the processor output signal into an acoustic output signal.

* * * * *